(12) United States Patent
Passaniti et al.

(10) Patent No.: US 11,391,686 B2
(45) Date of Patent: Jul. 19, 2022

(54) METHOD OF COUNTERING CONTAMINATION IN GAS SENSORS, CORRESPONDING CIRCUIT, DEVICE AND COMPUTER PROGRAM PRODUCT

(71) Applicant: STMicroelectronics S.r.l., Agrate Brianza (IT)

(72) Inventors: Fabio Passaniti, Syracuse (IT); Enrico Rosario Alessi, Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 257 days.

(21) Appl. No.: 16/566,069

(22) Filed: Sep. 10, 2019

(65) Prior Publication Data
US 2020/0088667 A1   Mar. 19, 2020

(30) Foreign Application Priority Data
Sep. 13, 2018   (IT) .......................... 102018000008567

(51) Int. Cl.
  *G01N 27/12*   (2006.01)
  *G01N 33/00*   (2006.01)
  *H05B 1/02*    (2006.01)

(52) U.S. Cl.
  CPC ......... *G01N 27/123* (2013.01); *G01N 33/007* (2013.01); *H05B 1/0283* (2013.01)

(58) Field of Classification Search
  CPC ........ G01N 21/88; G01N 21/94; G01N 21/85; G01N 2021/945; G01N 27/4077; G01N 27/4118; G01N 2021/745; G01N 23/20033; G01N 25/4826; G01N 2030/3053;
  (Continued)

(56) References Cited

U.S. PATENT DOCUMENTS

2002/0168772 A1 * 11/2002 Lloyd .................. G01N 33/007
                                                              436/37

FOREIGN PATENT DOCUMENTS

JP   2003344342 A   12/2003
JP   2016145738 A    8/2016

OTHER PUBLICATIONS

EPO Search Report and Written Opinion for co-pending EP Appl. No. 19195724.0 dated Jan. 30, 2020 (8 pages).

(Continued)

*Primary Examiner* — John Fitzgerald
*Assistant Examiner* — Truong D Phan
(74) *Attorney, Agent, or Firm* — Crowe & Dunlevy

(57) ABSTRACT

A sensor is driven at a first heating power value. The sensor generates a sensing signal that is indicative of a sensed entity. A possible onset of a sensor contamination condition is detected as a function of the sensing signal generated by the sensor. If such detecting fails to indicate onset of a sensor contamination condition, the sensor continues to be driven at the first heating power value. However, if such detecting indicates onset of a sensor contamination condition, a protection mode is activated. In the protection mode, the sensor is driven at a second heating power value for a protection interval, where the second heating power value is lower than the first heating power value. Furthermore, the operation may refrain from supplying power to the sensor for a further protection interval, wherein the further protection interval is longer than the protection interval.

26 Claims, 6 Drawing Sheets

(58) Field of Classification Search
CPC ....... G01N 2035/00346; G01N 27/123; G01N 27/124; G01N 33/007; H05B 1/0283
See application file for complete search history.

(56) References Cited

OTHER PUBLICATIONS

IT Search Report and Written Opinion for IT Appl. No. 102018000008567 dated May 28, 2019 (28 pages).
Schuler, M., et al: "A Novel Approach for Detecting HMDSO Poisoning of Metal Oxide Gas Sensors and Improving Their Stability by Temperature Cycled Operation," AMA Association for Sensor Technology, J. Sens. Sens. Syst., 4, 305-311, 2015.
Daniel Ruffer: "New Digital Metal-Oxide (MOx) Sensor Platform", Sensors, vol. 18, No. 4, Mar. 31, 2018, pp. 1-12, XP055574523.
Einollahi, Ayoub: "Selectivity Enhancement for a Temperature Modulated Electronic Nose Using Phase Space and Dynamic Moments," OREBRO University International Master's Thesis, 2012, 79 pages.
Palmisano, V., et al.: "Selectivity and resistance to poisons of commercial hydrogen sensors", International Journal of Hydrogen Energy, vol. 40, No. 35, Sep. 1, 2015, pp. 11740-11747.
Vergara, Alexander, et al: "Review Article: Optimized Feature Extraction for Temperature-Modulated Gas Sensors," Journal of Sensors, vol. 2009, Article ID 716316, 10 pages.

\* cited by examiner

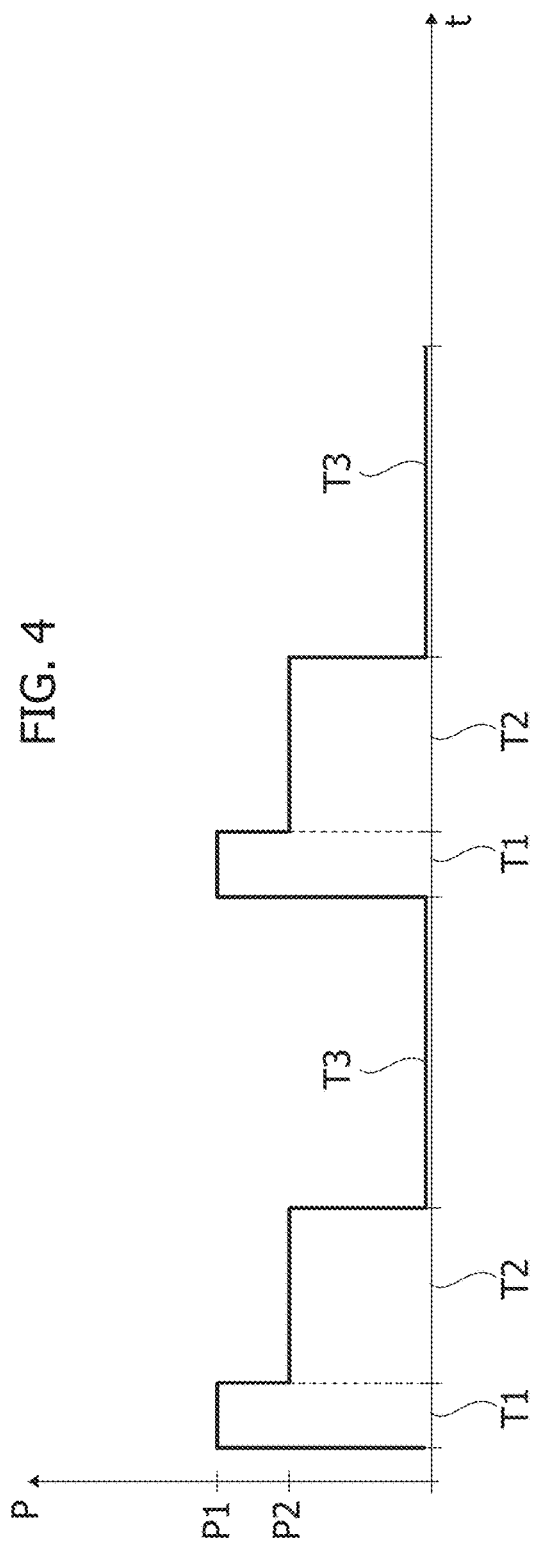
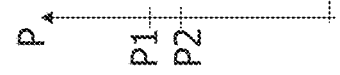
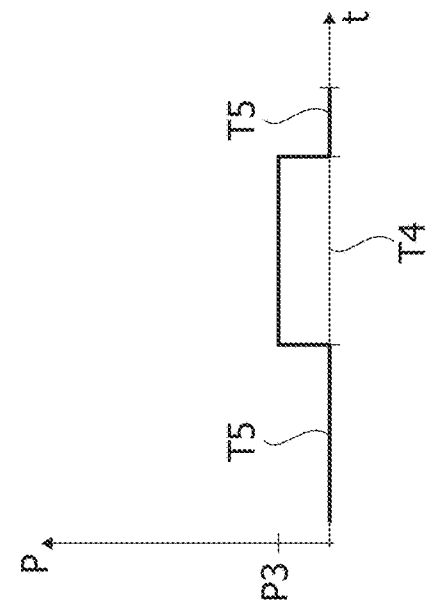

METHOD OF COUNTERING CONTAMINATION IN GAS SENSORS, CORRESPONDING CIRCUIT, DEVICE AND COMPUTER PROGRAM PRODUCT

PRIORITY CLAIM

This application claims the priority benefit of Italian Application for Patent No. 102018000008567, filed on Sep. 13, 2018, the content of which is hereby incorporated by reference in its entirety to the maximum extent allowable by law.

TECHNICAL FIELD

The description relates to protecting gas sensors from contaminants.

Gas sensors such as Metal Oxide (MOX) based gas sensors exposed to contamination that may degrade sensor performance (e.g., sensor response time and sensitivity) are exemplary of gas sensors to which embodiments may be applied.

BACKGROUND

Gas sensors based on metal oxide semiconductors (MOX) are conventionally applied to detection of target gases via redox reactions that occur between the target gases and an oxide surface of the sensors.

These reactions may occur at high temperatures and include two steps:
- redox reactions, during which oxygen ions $O^-$ distributed on the oxide surface of the gas sensor reacts with molecules of target gases, leading to an electronic variation of the oxide surface, and
- a transduction step during which the redox reactions are transduced into an electrical resistance variation of the gas sensor.

Ideally, the MOX sensing element (i.e., the oxide surface) should be maintained active at a desired working temperature (pre)defined for a specific target gas and application. The main power consumption of the gas sensor may thus be due to a micro-hot plate MHP in the gas sensor, which provides heat to the sensing element. In case of wearable and portable devices, limitations to such power consumption may be desirable.

It is noted that MOX-based gas sensors may be affected by the presence of contaminants, e.g., siloxanes, that exhibit a "poisoning" effect. This may lead to degradation of sensor performance in terms of sensitivity and response time. For instance, contaminants may be present in wearable or portable devices and their accessories and such presence may affect penetration of the gas sensors in this market.

Also, siloxane is present in the environment, see e.g., Tran T. M. et al., "Occurrence of cyclic and linear siloxanes in indoor air from Albany, N.Y., USA, and its implications for inhalation exposure", Science of The Total Environment, Volume 511, 1 Apr. 2015, Pages 138-144. This document discloses siloxane concentrations collected in 60 indoor air samples in New York, wherein an average of 0.096 ppb was found, e.g., 0.016 ppb in laboratories and 0.40 ppb in salons.

Meng F., et al., "Indoor Air Pollution by Methylsiloxane in Household and Automobile Settings", PLoS ONE 10(8): e0135509 (2015) disclose a study of total siloxane concentration collected from 40 family homes undergoing redecoration in the Beijing area, resulting in an average of 0.69 ppb.

It is noted that even a phone cover can be source of cyclosiloxane vapors of hexamethyl cyclotrisiloxane (D3), octamethyl cyclotetrasiloxane (D4) and decamethyl cyclopentasiloxane (D5). Such compounds may have a degradation effect on the gas sensor in terms of sensitivity and response time. For example, if a gas sensor is exposed to D5 siloxane for 1 hour at 200 ppm (parts per million), the MOX resistance does not react with same speed and sensitivity to 10 ppm of ethanol with respect to a MOX resistance before exposure to siloxane.

Accordingly, an improved solution is desired which would be able to detect the presence of sensor poisoning by siloxanes.

SUMMARY

There is a need for protecting gas sensors from siloxane contamination and degradation. In one or more embodiments this need is addressed by means of a method having the features set forth in the claims that follow.

One or more embodiments may include a corresponding circuit (e.g., a circuit for driving the sensor and for receiving therefrom a sensing signal) and a corresponding device.

A portable device including a MOX gas sensor may be exemplary of such a device.

One or more embodiments may include a computer program product loadable in the memory of at least one processing module (e.g., processing circuitry of a circuit or a device according to one or more embodiments) and including software code portions for executing the steps of the method when the product is run on at least one processing module. As used herein, reference to such a computer program product is understood as being equivalent to reference to a computer-readable means containing instructions for controlling the processing system in order to co-ordinate implementation of the method according to one or more embodiments. Reference to "at least one computer" is intended to highlight the possibility for one or more embodiments to be implemented in modular and/or distributed form.

The claims are an integral portion of the disclosure of the invention as provided herein.

One or more embodiments may exhibit one or more advantages, for example:
- low power consumption,
- low computational load,
- adaptive reaction to status of contamination,
- possibility of compensating a sensitivity drop adaptively, and
- by recognizing the status of contamination, the possibility exists to mark records of the gas sensor as "affected by contamination" for post processing.

One or more embodiments may apply to gas modules in low-power, low-latency devices, e.g., portable devices such as mobile phones, handled devices or wearable devices, which may be used for air quality detection in closed environments such as homes or vehicles.

One or more embodiments may apply to the field of environmental sensors in the consumer, automotive, industrial and medical markets as well as for IoT (Internet of Things) nodes.

In an embodiment, a method comprises: driving a sensor by supplying to the sensor a first heating power value; receiving from the sensor a sensing signal indicative of a sensed entity; detecting, as a function of the sensing signal from the sensor, a (possible) onset of a sensor contamination condition; continuing supplying to the sensor the first heating power value if said detecting fails to indicate onset of the sensor contamination condition; activating a protection mode if said detecting indicates onset of the sensor contamination condition. The protection mode comprises: supplying to the sensor a second heating power value for a protection interval, wherein the second heating power value is lower than the first heating power value.

One or more embodiments may comprise refraining from supplying power to the sensor for a further protection interval, wherein the further protection interval is longer, optionally substantially longer, than said protection interval.

The sensing signal from the sensor may be indicative of a resistance value of the sensor and said driving the sensor by supplying to the sensor the first heating power value may comprise intermittently supplying to the sensor the first heating power value for a plurality of time intervals. Detecting onset of the sensor contamination condition may comprise: sensing, as a function of the sensing signal from the sensor, a plurality of resistance values of the sensing signal at the ends of the time intervals in the plurality of time intervals; calculating, as a function of the sensing signal from the sensor, a plurality of slope values indicative of the behavior of the sensing signal over the time intervals in the plurality of time intervals; checking the resistance values and the slope values against a reference template; and declaring onset of the contamination condition if the resistance values and the slope values fail to comply with the reference template.

Further to the foregoing, a plot of the slope values against the resistance values may be generated, wherein the plot may be aligned with an alignment direction; the alignment direction may be checked for matching with a reference alignment direction; and the onset of the contamination condition is declared if the alignment direction fails to match with the reference alignment direction.

Activation of the protection mode as a result of detecting onset of a sensor contamination condition may comprise: supplying to the sensor the first heating power value for at least one respective time interval following said protection interval; checking whether a contamination condition persists at the end of the at least one respective time interval; resuming supplying to the sensor the first heating power value if the checking fails to indicate a sensor contamination condition persisting; and activating again the protection mode if the checking indicates a sensor contamination condition persisting.

Further to the foregoing, the alignment direction leading to the protection mode being activated as a result of detecting onset of a sensor contamination condition may be stored; the first heating power value may be intermittently supplied for a second plurality of time intervals following the protection interval; and the sensing signal may be received from the sensor over the second plurality of time intervals. Checking whether a contamination condition persists at the end of the second plurality of time intervals comprises: sensing, as a function of the sensing signal from the sensor, a plurality of resistance values of the sensor at the ends of the time intervals in the second plurality of time intervals; calculating, as a function of the sensing signal from the sensor, a plurality of slope values indicative of the behavior of the sensing signal over the time intervals in the second plurality of time intervals; generating a respective plot of the slope values against the resistance values for the time intervals in the second plurality of time intervals, wherein the plot may be aligned with a respective alignment direction; comparing the respective alignment direction with the alignment direction stored; and declaring a contamination condition persisting at the end of said second plurality of time intervals as a function of the result of the comparing.

A contamination condition persisting at the end of the second plurality of time intervals is declared if the respective alignment direction is aligned to the alignment direction stored or diverges therefrom away from said reference alignment direction (e.g., if the alignment direction calculated during the protection mode is equal to or lower than the stored alignment direction in a plot).

The method further comprises resuming supplying to the sensor the first heating power value after activating a protection mode and checking whether a contamination condition persists as a result of activation of said protection mode. Resuming may comprise, prior to resuming supplying to the sensor the first heating power value, performing a sensor warm-up sequence comprising: i) supplying to the sensor said first heating power value for a resumption interval; and ii) refraining from supplying power to the sensor for a further resumption interval.

For instance, the sensor warm-up sequence comprises: supplying to the sensor said first heating power value for a first resumption interval; supplying to the sensor a resumption power value for a second resumption interval, wherein the resumption power value is different from the first heating power value; and refraining from supplying power to the sensor for a third resumption interval.

Operation for supplying to the sensor said first heating power value—in the normal mode and/or in other modes (such as the resumption mode)—may comprise a supply profile comprising said first heating power value as a peak value and (at least one) second heating power value different from said first heating power value.

In an embodiment, a circuit comprises: at least one input node configured to receive from a sensor a sensing signal indicative of a sensed entity; at least one power node configured to power the sensor; processing circuitry coupled with the at least one input node and the at least one power node and configured to perform the steps of the method as previously described.

In an embodiments, a device comprises: at least one sensor, such as a gas sensor, for example a metal oxide semiconductor gas sensor, producing a sensing signal indicative of sensed entity; a circuit as previously described, arranged with the at least one input node coupled to the sensor to receive the sensing signal therefrom and the at least one power node coupled to the sensor for powering the sensor.

In an embodiment, a computer program product, loadable in the memory of the processing circuitry in a circuit or a device as described above, includes software code portions that are executable on the processing circuitry for performing the method according to the method described above.

BRIEF DESCRIPTION OF THE DRAWINGS

One or more embodiments will now be described, by way of example only, with reference to the annexed figures, wherein:

FIGS. 4 to 6 represent non-limiting examples of possible driving profile for a gas sensor according to one or more embodiments.

DETAILED DESCRIPTION

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

As discussed previously, gas sensors such as Metal Oxide MOX-based gas sensors may be exposed to contamination that may degrade sensor performance.

Related issues have already been investigated, as witnessed by documents such as:

A. Einollahi, "Selectivity Enhancement for a Temperature Modulated Electronis Nose using Phase Space and Dynamic Moments", International Master's Thesis, Studies from the Department of Technology at Orebro University, Orebro 2012, or M. Schiller, et al., "A novel approach for detecting HDMSO poisoning of metal oxide gas sensors and improving their stability by temperature cycled operations", J. Sens. Sens. Syst, 4, 305-311, 2015.

Figure 1:
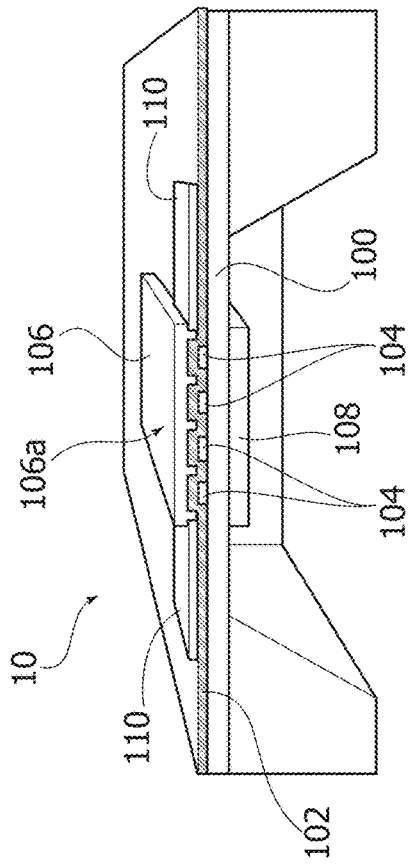
FIG. 1 shows a non-limiting example of a gas sensor according to one or more embodiments.

FIG. 1 shows an example of a MOX-based gas sensor 10, e.g., comprising one or more gas sensing elements in MOX—metal oxide—technology. Such an exemplary sensor 10 may comprise:

a micro-hot plate MHP, a silicon substrate 108, and two electrodes 110, arranged substantially sidewise of the layer of metal oxide sensing material 106, e.g., on opposite lateral sides thereof.

In one or more embodiments, the micro-hot plate MHP may comprise a membrane 100, e.g., suspended in order to facilitate good thermal dissipation and isolation, a layer of electrical insulating material 102 and one or more heater elements 104 (e.g., platinum resistances) arranged thereon. Also, the micro-hot plate may comprise a layer of MOX sensing material 106 (e.g., tin dioxide—$SnO_2$) arranged over the heater element(s) 104.

As exemplified in FIG. 1, the layer of electrical insulating material 102 of the micro-hot plate MHP may be arranged between the heater(s) 104 plus the membrane 100 and the layer of MOX sensing material 106.

The MOX sensing material may be provided onto the electrical insulating layer 102 by resorting to specific techniques (known to those of skill in the art), for example micro-dispensing or screen printing. Also, the heater(s) 104 may be sandwiched between the electrical insulating layer 102 and the membrane 100.

In one or more embodiments, the layer of MOX sensing material 106 may have a front surface 106a, opposite to a surface of the layer of MOX sensing material 106 facing towards the heater(s) 104, which may be exposed to air and may sense a target gas, e.g., a volatile organic compound—VOC, if present.

As already discussed, the MOX conductance may change value proportionally to the VOC concentration at working temperatures. For example, the gas sensor 10 may provide a sensing signal, e.g., a resistance signal, which may be indicative of the presence of one or more target gases, wherein the resistance may decrease when the concentration of the target gas may increase.

In one or more embodiments, the VOC concentration may be calculated as a function of the variation of the MOX resistance signal in the presence of a VOC with respect to the MOX resistance signal in clean air. A calibration of the MOX sensing material, at specific working conditions, may enable to translate this ratio into gas concentration (ppb, parts per billion, or ppm, parts per million).

In one or more embodiments, the two electrodes 110 may be placed onto the electrical insulating layer 102, at opposite lateral surfaces of the layer of MOX sensing oxide 106, with the two electrodes 110 electrically connected to the layer of MOX sensing material 106. The two electrodes 110 may be configured to obtain the MOX resistance value from the MOX sensing material 106 and, e.g., after calibration, such value may be converted in gas concentration.

In one or more embodiments, the heater(s) 104 arranged below the layer of MOX sensing material 106 may facilitate heating the layer of MOX sensing material 106 to one or more desired working temperature values, for example between 350-400° C., and maintaining such values during operation of the sensor 10.

The micro-hot plate may be cyclically (possibly continuously) heated up to 450° C.: accordingly, the heated layer of MOX sensing material 106 may be reactive and sensitive to the presence of a target gas, e.g., volatile organic compounds VOC such as ethanol, toluene, benzene, formaldehyde. Intermittent heating of the micro-hot plate represents a conventional approach used for reducing the power consumption of the gas sensors: a micro-hot plate may be alternatively powered by a pulse switching on and off over time, i.e. a pulse switching between high and low values. A trade-off between level power consumption and performance (e.g., accuracy, sensitivity and stability) may be achieved capable of countering degradation of the gas sensor, e.g., by reducing the duty cycle and/or the current level.

Figure 2:
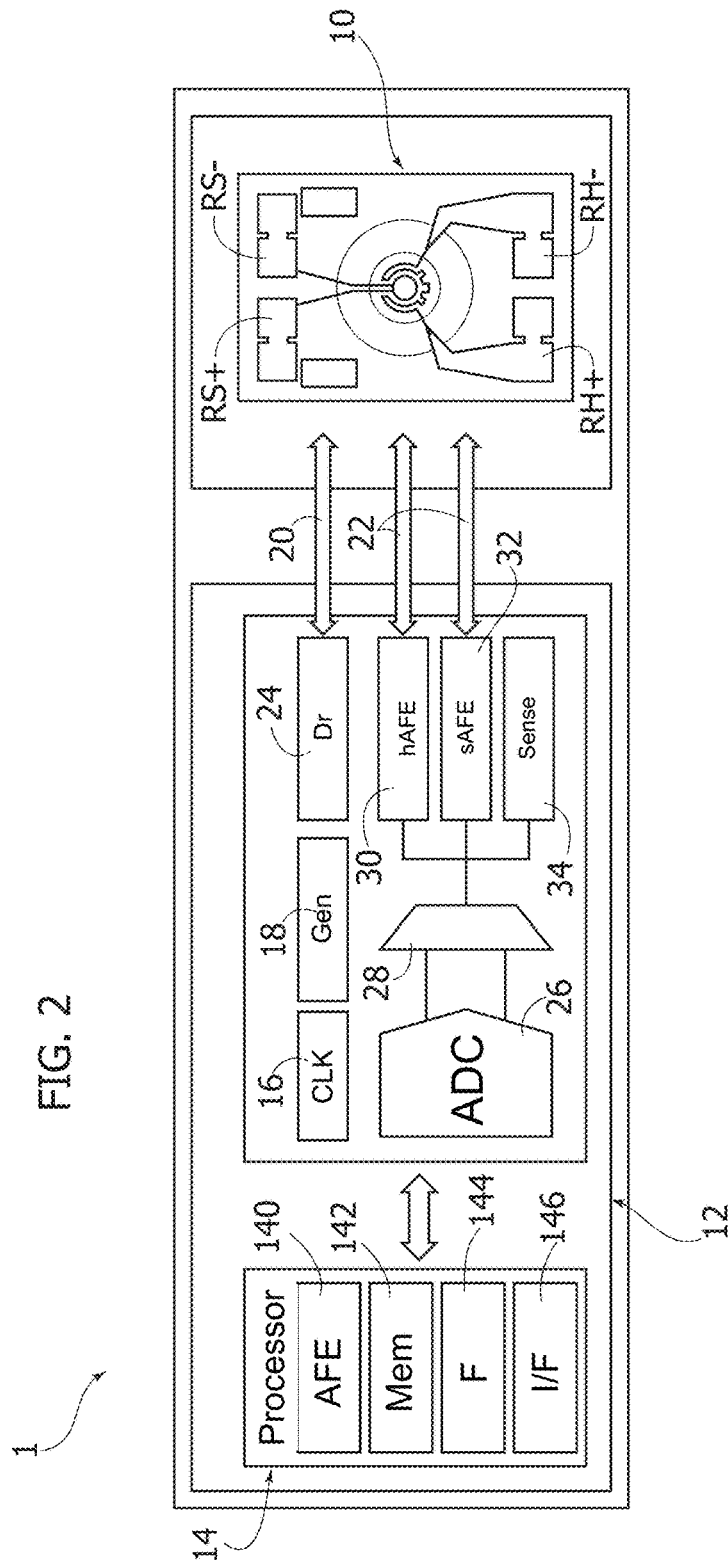
FIG. 2 shows a non-limiting example of a device including the gas sensor according to one or more embodiments.

As already discussed, one or more gas sensors 10 may be comprised in a portable device 1, exemplified in FIG. 2. The portable device 1 in FIG. 2 may comprise a sensor 10 as discussed previously and an (e.g., application-specific) integrated circuit 12, wherein the integrated circuit 12 is coupled to the sensor 10 and may be configured to perform the steps of the method according to one or more embodiments. The integrated circuit 12 may comprise a processor circuit 14 suited to be coupled to power nodes 20 and input nodes 22, and which can be configured to supply power to the sensor 10 (via nodes 20) and to receive (via nodes 22) signals indicative of an event produced by the sensor 10, e.g., for receiving the sensing data therefrom. Corresponding terminals may be found in the sensor 10: e.g., power terminals RH+, RH− and sensing terminals RS+, RS− to be connected to the power nodes 20 and input nodes 22 of the circuit according to one or more embodiments.

FIG. 2 shows various other elements which, in one or more embodiments, may be included in the circuit 12. For instance, the processor circuit 14 may comprise a digital front-end, e.g., comprising a phase generator from the analog front-end (AFE) 140, one or more memories (Mem) 142, one or more digital filters (F) 144 and one or more I2C/SPI interfaces (I/F) 146.

In one or more embodiments, the circuit 12 may comprise further elements involved in operating the sensor 10. The following designations may apply to the blocks shown in the integrated circuit 12:

- 16: clock (CLK);
- 18: reference current/voltage generator (Gen);
- 24: heater current driver (Dr);
- 26: analog-to-digital converter (ADC);
- 28: multiplexer;
- 30: heater analog front-end (hAFE);
- 32: sense analogue front-end (sAFE); and
- 34: heater and humidity H/T sensor (Sense); this may be arranged in an opposite position of the device 1 with respect to the sensor 10, in order to facilitate avoiding interferences therewith.

One or more embodiments may thus relate to a method for detecting contamination (e.g., due to the presence of siloxanes in the air) of the MOX-based gas sensor 10. The method may comprise determining that a contamination condition is present and acting accordingly, e.g., by operating the sensor 10 in a protective mode. For example, the sensor 10 may be operated in a normal mode if no contamination is detected, and in a protection mode if a contamination is detected. Also, a further mode may be present, a recovery mode, that may be used after a contamination condition disappears and before a normal mode is resumed.

Figure 3:
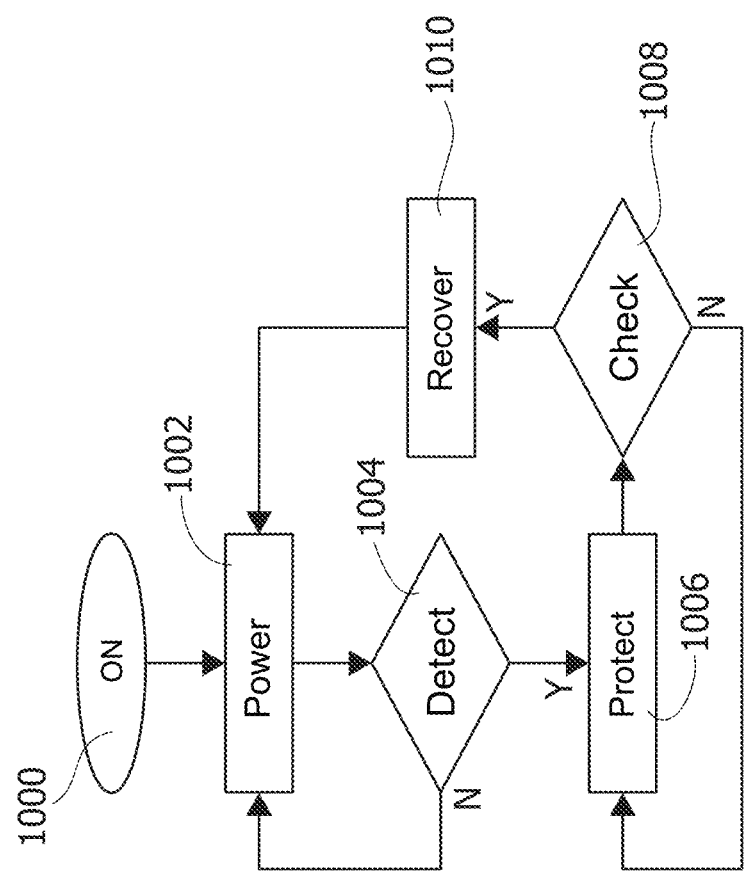
FIG. 3 represents a non-limiting example of a flow chart comprising the steps of a method according to one or more embodiments.

With reference to FIG. 3, after the sensor 10 is switched on (act 1000), the sensor 10 may operate in a normal mode comprising supplying power (act 1002) to the sensor 10 according to a normal power profile. For example, the normal mode may comprise a pulsed mode or a continuous mode, or may comprise different current profiles for heating the micro-hot plate MHP.

As exemplified in FIG. 4, an intermittent heating profile may be used as the normal power profile, wherein each cycle may comprise, for instance:

- a first heating power value P1 applied to the sensor 10 for a first time interval T1 (e.g., 0.5 s),
- a second heating power value P2, different from (e.g., smaller than) the first heating power value P1, applied to the sensor 10 for a second time interval T2 (e.g., 4.5 s), the second time interval T2 being different from (e.g., longer than) the first time interval T1, and
- no power applied to the sensor 10 for a third time interval T3 (e.g., 55 s) that may be longer than the first and second time interval T1 and T2.

One or more embodiments as exemplified herein may thus comprise supplying to the sensor the first heating power value (that is, P1) with a supply profile as shown in FIG. 4, that is a supply profile comprising the first heating power value P1 as a peak value and (at least one) second heating power value, such as P2, different from (lower than) the first heating power value P1.

In one or more embodiments as exemplified herein, the first heating power value P1 and the second heating power value P2 may represent leading and trailing portions, respectively, of the heating power pulses applied to the sensor 10.

It will be otherwise understood that the heating power profile exemplified herein may vary, even appreciably, insofar as the normal mode power profile may depend on the MOX-based gas sensor 10 employed and the application specific constraints. For example, the normal power profile may be modified based on the gas sensor 10 employed in order to obtain a trade-off between sensitivity performance plus time response and power consumption.

For that reason, the first heating power value P1 will be primarily referred to in the following for the sake of simplicity and ease of explanation, being otherwise understood that the (average) heating power applied to the sensor 10 will be a function of the first heating power value P1, the function being dictated by the heating power profile (e.g., P1 over T1, P2 over T2, an so on) adopted.

In one or more embodiments, during normal mode, the sensor 10 may thus be operated with the normal power profile (act 1002), and the method may comprise detecting (that is, checking or investigating—act 1004) whether a contamination has occurred, for example due to presence of siloxanes.

In one or more embodiments, a contamination condition may be detected as a function of a sensor response received, e.g., a resistance response that may vary as a function of the presence of a target gas and/or contaminants such as siloxanes as better described in the following.

If no contamination is detected (act 1004, N), the sensor 10 may continue to operate in the normal mode.

Conversely, if the check (act 1004) indicates that a contamination has occurred (act 1004, Y), a protection mode may be activated (act 1006).

In one or more embodiments, the protection mode may be regarded as related to the MOX sensing material 106.

For example, during the protection mode, the sensor 10 may be driven so that the sensor 10 may be only poorly (if hardly) affected by siloxanes or other contaminants.

For example, the protection mode may comprise, during a first phase, intermittently (e.g., cyclically) applying to the sensor 10 an (ultra)low power mode and protection power profile as exemplified in FIG. 5, comprising:

- a third power value P3, smaller than the first (and second) power values P1 (and P2)—e.g. a low level of current for the micro-hot plate heating—applied to the sensor 10 for a (fourth) time interval T4 (e.g., 5 s) that may optionally comprise the sum of the first and second time interval T1 and T2, and, optionally (that is, non-mandatory);
- no power applied to the sensor 10 for a (fifth) time interval T5.

Stated otherwise, in one or more embodiments (hence the wording "optionally") the time interval T5 might have zero duration, with the power value P3 applied over a time interval T4 of (notionally) indefinite duration.

After a predetermined time has elapsed, e.g., after 5 minutes, a recovery power profile may be intermittently supplied to the sensor 10, wherein each cycle may comprise:

- the first heating power value P1 applied to the sensor 10 for the first time interval T1 (e.g., 0.5 s),
- the second heating power value P2 applied to the sensor 10 for the second time interval T2 (e.g., 4.5 s), and no power applied to the sensor 10 for a (sixth) time interval T6, with the time interval T6 which may be substantially smaller than the time interval T3.

That is, the recovery power profile may substantially correspond to the normal power profile, with however the time interval T6 that may be significantly smaller (e.g., ten times smaller) than the time interval T3.

As for the rest, the same points discussed previously in respect of the possible profile of applying the first heating power value P1 in the "normal" operation mode may apply also to the recovery mode.

In one or more embodiments, the recovery power profile may be applied to the sensor 10 for a predetermined number of times, before checking (act 1008) whether a contamination condition persists for the sensor 10, with the checking being based on the sensor response due to the recovery power profile.

If contamination persists (act 1008, N), the sensor 10 may continue to operate in protection mode, e.g., the sensor 10 may return to be operated using the protection power profile (act 1006). Conversely, if the check (act 1008) indicates that a contamination is absent (act 1004, Y), the method may return to normal mode (1002).

Optionally, in one or more embodiments, a recovery mode (act 1010) may be activated at the end of the protection mode, before returning to the normal mode, which may facilitate accelerating the recovery of the sensor 10, exposed to siloxane contamination, to return to an initial, non-contaminated performance of the MOX gas sensor 10.

In recovery mode (act 1010), the intermittent heating power profile applied to the sensor 10 may comprise the recovery power profile that may be employed also in the protection mode (see FIG. 6), wherein:

the first heating power value P1 may be applied to the sensor 10 for the first time interval T1 (e.g., 0.5 s), the second heating power value P2 may be applied to the sensor 10 for the second time interval T2 (e.g., 4.5 s), and no power may be applied to the sensor 10 for the time interval T6, with the time interval T6 that may be substantially smaller than the time interval T3.

Figure 7:
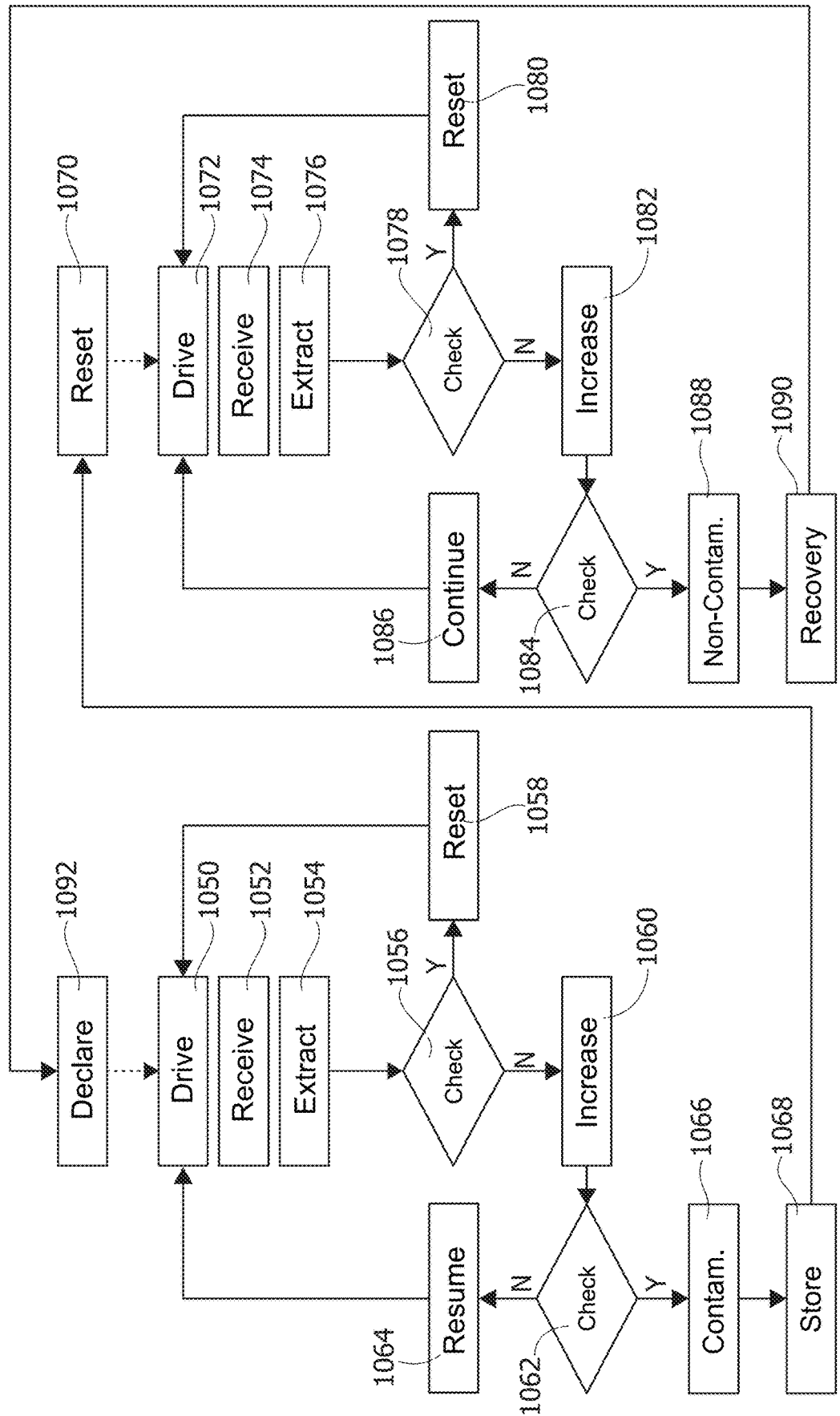
FIG. 7 represents a non-limiting example of a flow chart comprising the steps of a method according to one or more embodiments, FIG. 8 exemplifies a possible response of a gas sensor according to one or more embodiments, and FIGS. 9A-9B exemplify plots comprising certain features of a resistance response of a sensor according to one or more embodiments.

In one or more embodiments, the method for determining (e.g., siloxane) contamination in a MOX-based sensor 10 may comprise, as illustrated in FIG. 7:

intermittently driving (act 1050) the micro-hot plate of the sensor 10 using the normal power profile exemplified in FIG. 4, e.g., for a first plurality of cycles, receiving (act 1052) a sensor response, e.g., a resistance signal, comprising, for each cycle, a first subset and a second subset corresponding to the sensor response during the first time interval T1 and the second time interval T2, respectively, extracting (act 1054), from the first subset of the sensor response, resistance values at the ends of the first time intervals T1 and slope values indicative of the behavior of the sensor response during the first time intervals T1, checking (act 1056), as a function of the resistance values and the rising slope values, as better described in the following, if a contamination condition of the MOX-based gas sensor 10 is present, if the contamination condition is not present (act 1056, N; act 1058), resetting a contamination count and resuming operating the gas sensor 10 with the normal power profile (act 1050), if the contamination condition is present (act 1056, Y; act 1060), increasing the contamination count, checking (act 1062) if the contamination count has reached a predetermined threshold, e.g., if a contamination was found to be present for more than 3 times, if the contamination count has not reached the predetermined threshold (act 1062, N; act 1064), resuming operating the gas sensor 10 with the normal power profile (act 1050), if the contamination count has reached the predetermined threshold (1062, Y; act 1066), declaring the MOX-gas sensor 10 as under contamination, storing (act 1068) features indicative of the contamination, e.g., the resistance values and the slope values, that led to the contamination condition being detected, resetting (act 1070) contamination parameters, e.g., a non-contamination count, intermittently driving (act 1072) the micro-hot plate of the sensor 10 using the protection power profile exemplified in FIG. 5 in a first phase and intermittently driving the micro-hot plate of the sensor 10 using the recovery power profile exemplified in FIG. 6, e.g., for a second plurality of cycles, in a second phase, receiving (act 1074) the sensor resistance response over the second plurality of cycles, the sensor response comprising, for each cycle, a first subset and a second subset corresponding to the sensor response during the first time interval T1 and the second time interval T2, respectively, extracting (act 1076), from the first subsets of the sensor response, further slope values indicative of the behavior of the sensor response over the first time intervals T1 and (further) resistance values at the ends of the first time intervals T1 of the sensor response, checking (act 1078), as a function of the further slope values and the further resistance values as well as the stored features e.g. stored slope values and resistance values as better described in the following, if the detected contamination condition of the MOX-based gas sensor 10 persists, if the contamination condition is still present (act 1078, N; act 1080), resetting the non-contamination count and continuing operating the gas sensor 10 in protection mode (act 1072), if the contamination condition results to be absent (act 1078, Y; act 1082), increasing the non-contamination count, checking (act 1084) if the non-contamination count has reached a further predetermined threshold, e.g., if a contamination was found to be absent for more than 3 times, if the non-contamination count has not reached the further predetermined threshold (act 1084, N; act 1086), continuing operating the gas sensor 10 in protection mode (act 1072), if the non-contamination count has reached the predetermined threshold (act 1084, Y; act 1088), declaring the MOX-gas sensor 10 as out of contamination, optionally performing (act 1090) a recovery mode as described previously, with the recovery mode comprising intermittently driving the micro-hot plate of the sensor 10 using the recovery power profile exemplified in FIG. 6, and declaring (act 1092) the sensor 10 as operating correctly and resetting the contamination count plus resuming operating the sensor 10 in normal mode (act 1050).

As already discussed, in one or more embodiments, during normal mode or protection mode, certain features may be extracted from the resistance response R of the sensor 10. The received resistance response R may comprise, for each cycle, a first subset received over the first time interval T1 and a second subset received over the second time interval T2, with the first subset being used for checking for contamination (if present or if persisting) and the second subset suitable to be used for determining the presence of one or more target gases and evaluating the concentration thereof.

Figure 8:
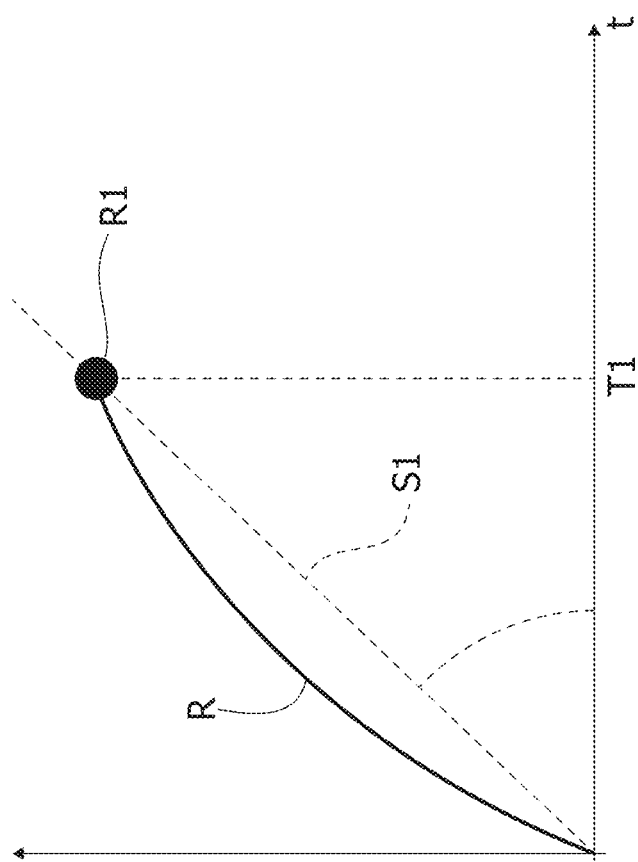

For example, considering an applied power profile such as the normal power profile of FIG. 4 or the recovery power profile of FIG. 6, the resistance response R over the first time interval T1 in a cycle may be as exemplified in FIG. 8. The resistance response R may comprise a rising behavior, and the features extracted may comprise a slope value S1 and a resistance value R1 at the end of the first time interval T1.

Figure 9B:
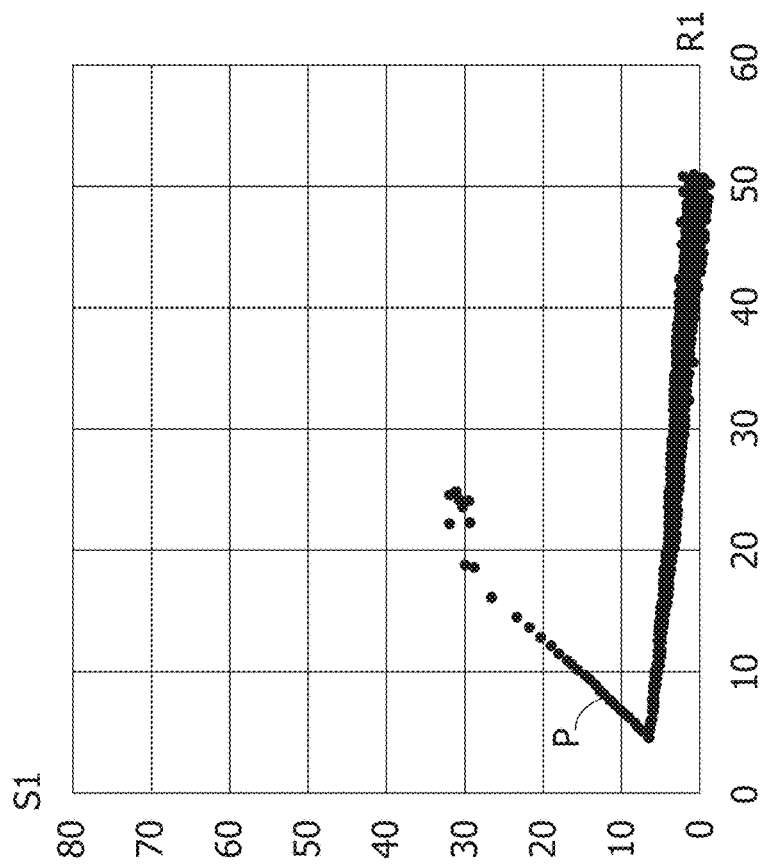
Figure 9A:
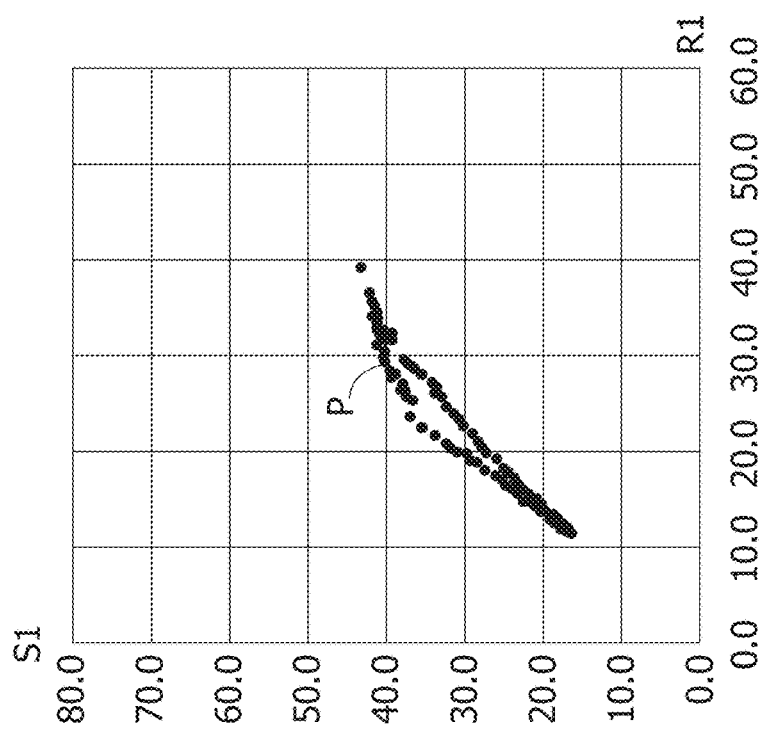

In one or more embodiments, the contamination check may be based on the analysis of these values depicted in a plot, exemplified in FIGS. 9A-9B. The plot may comprise a horizontal axis for the resistance values R1 of the resistance response R at the end of the first time intervals T1 of each cycle and a vertical axis for the slope values S1 of the sensing signal R of the first time intervals T1 of each cycle. Points P in the plot of FIGS. 9A and 9B, may be indicative of the values S1 versus R1 after each power supplying cycle (e.g., a normal power profile or a recovery power profile) supplied to the sensor 10.

In one or more embodiments, the points P in the plot, which are a function of the resistance values and the slope values S1 after each cycle, may form one or more alignment directions that may be calculated and that may be indicative of a possible contamination condition.

For instance, the plot shown in FIG. 9A exemplifies a gas sensor behavior according to one or more embodiments, when no contamination is present: the alignment orientation/trajectories of the points P in the plot may be regarded as substantially lying on a diagonal region of the plot, and the sensor 10 may be thus considered as non-contaminated.

Conversely, the plot shown in FIG. 9B exemplifies a gas sensor behavior according to one or more embodiments, when a contaminant, e.g., a siloxane, is present. For example, the plot may exhibit:

a first alignment orientation of the points P substantially along the diagonal line of the plot, that may be indicative of a variation of the resistance response R due to the presence of a target gas when no contamination is present, and a second alignment orientation of the points P, almost horizontal, that may be indicative of a contamination of the gas sensor 10 being present.

In one or more embodiments, checking whether a contamination condition is present may thus comprise checking whether the alignment orientation in the plot lie substantially at (around) the diagonal line of the plot, e.g., if the alignment orientation of the points P lies (possibly after normalization or scaling of the axes with respect to the highest values for R and S, as determined during calibration or final testing of the device) at about 45° with respect to the axes and/or if the alignment orientation of the points P reaches a predetermined lower threshold.

In one or more embodiments, after a contamination is detected, the protection mode may be activated and checking may be performed to determine if the detected contamination condition of the MOX-based gas sensor 10 persists or disappears. For example, such checking may comprise:

storing the calculated alignment orientation of the (last received) points P that led to the protection mode being activated, extracting, from the resistance response R of the sensor 10 received, e.g., following the recovery power profile being intermittently applied to the sensor 10 during the protection mode, further slope values S1 over the first time intervals T1 and resistance values R1 at the end of the first time intervals T1, calculating a further alignment orientation of further points P, based on the further received slope values S1 and resistance values R1 as already discussed, comparing the stored alignment orientation against the further alignment orientation, and if the stored alignment orientation that led to the protection mode being activated is lower than the further alignment orientation calculated during the protection mode, a non-contamination condition may be declared.

In one or more embodiments, the possibility exists of checking whether a certain distance is present between two adjacent points P of the plot. For example, if a horizontal distance between two adjacent points P is lower than a certain threshold, the alignment orientation of the points P may not be calculated thereon and new values may be desirable for an improved detection of contamination.

Accordingly, in one or more embodiments, checking whether a contamination condition is present (act 1056) or persisting (act 1078) may also comprise checking if a lower distance is present between pairs of adjacent points P (e.g., adjacent horizontally, that is with a lower distance of resistance value R1 being present between the points P) and:

if a lower distance between adjacent points P is not reached, detecting if the alignment orientation of the points P reaches a predetermined lower threshold, and if the lower distance between adjacent points P is reached, resuming performing power supplying and feature extraction cycles (acts 1050-1054 or 1072-1076) to obtain new improved values.

One or more embodiments may thus relate to a method comprising:

driving (e.g., 1002, 1050) a sensor (e.g., 10) by supplying to the sensor a first heating power value (e.g., P1, possibly with a certain profile, e.g. P1, T1; P2, T2 as exemplified in FIG. 4), receiving (e.g., 1052) from the sensor a sensing signal (e.g., R) indicative of a sensed entity, detecting (that is, investigating, e.g., 1004, 1056), as a function of the sensing signal from the sensor, (possible) onset of a sensor contamination condition, if said detecting fails to indicate onset of a sensor contamination condition (e.g., 1004, N; 1056, N) continuing supplying to the sensor the first heating power value, if said detecting indicates onset of a sensor contamination condition (e.g., 1004, Y; 1056, Y) activating a protection mode (e.g., 1006, 1072), the protection mode comprising supplying to the sensor a second heating power value (e.g., P3) for a protection interval (e.g., T4), the second heating power value lower than the first heating power value.

One or more embodiments may comprise refraining from supplying power to the sensor for a further protection interval (e.g., T5), the further protection interval being longer, optionally substantially longer (e.g., ten times longer) than said protection interval.

In one or more embodiments, the sensing signal from the sensor may be indicative of a resistance value of the sensor and said driving the sensor by supplying to the sensor the first heating power value may comprise intermittently supplying to the sensor the first heating power value for a plurality of time intervals (e.g., T1), wherein detecting (e.g., 1004, 1056) onset of a sensor contamination condition may comprise:
- sensing (e.g., 1052), as a function of the sensing signal from the sensor, a plurality of resistance values (e.g., R1) of the sensing signal at the ends of the time intervals in the plurality of time intervals,
- calculating (e.g., 1054), as a function of the sensing signal from the sensor, a plurality of slope values indicative of the behavior of the sensing signal over the time intervals in the plurality of time intervals,
- checking (e.g., 1056) the resistance values and the slope values against a reference template (e.g., a diagonal of a plot according to FIG. 9), and
- declaring (e.g., 1066) onset of a contamination condition if the resistance values and the slope values fail to comply with the reference template.

One or more embodiments may comprise:
- generating a plot (see, e.g., FIG. 9) of the slope values against the resistance values, wherein the plot may be aligned with an alignment direction,
- checking whether the alignment direction matches with a reference alignment direction (e.g., a diagonal of the plot), and
- declaring onset of a contamination condition if the alignment direction fails to match with the reference alignment direction.

In one or more embodiments, the protection mode activated as a result of detecting onset of a sensor contamination condition may comprise:
- supplying (e.g., 1006, 1072) to the sensor the first heating power value for at least one respective time interval (e.g., T1) following said protection interval,
- checking (e.g., 1008, 1078) whether a contamination condition persists at the end of the at least one respective time interval,
- if the checking fails to indicate a sensor contamination condition persisting (e.g., 1008, Y; 1078, Y), resuming supplying to the sensor the first heating power value,
- if the checking indicates a sensor contamination condition persisting (e.g., 1008, N; 1078, N), activating again the protection mode.

One or more embodiments may comprise:
- storing (e.g., 1068) the alignment direction leading to the protection mode being activated as a result of detecting onset of a sensor contamination condition,
- intermittently supplying to the sensor the first heating power value for a second plurality of time intervals (e.g., T1) following the protection interval,
- receiving from the sensor the sensing signal over the second plurality of time intervals, wherein said checking whether a contamination condition persists at the end of the second plurality of time intervals may comprise:
- sensing (e.g., 1074), as a function of the sensing signal from the sensor, a plurality of resistance values of the sensor at the ends of the time intervals in the second plurality of time intervals,
- calculating (e.g., 1076), as a function of the sensing signal from the sensor, a plurality of slope values indicative of the behavior of the sensing signal over the time intervals in the second plurality of time intervals,
- generating a respective plot of the slope values against the resistance values for the time intervals in the second plurality of time intervals, wherein the plot may be aligned with a respective alignment direction,
- comparing the respective alignment direction with the alignment direction stored; and
- declaring a contamination condition persisting at the end of said second plurality of time intervals as a function of the result of the comparing.

One or more embodiments may comprise declaring a contamination condition persisting at the end of the second plurality of time intervals if the respective alignment direction is aligned to the alignment direction stored or diverges therefrom away from said reference alignment direction (e.g., if the alignment direction calculated during the protection mode is equal to or lower than the stored alignment direction in a plot such as that of FIG. 9).

One or more embodiments may comprise resuming supplying to the sensor the first heating power value after activating a protection mode and checking whether a contamination condition persists as a result of activation of said protection mode, wherein said resuming may comprise, prior to resuming supplying to the sensor the first heating power value, a sensor warm-up sequence (e.g., 1010, 1090) comprising:
- i) supplying to the sensor said first heating power value for a resumption interval (e.g., T1),
- ii) refraining from supplying power to the sensor for a further resumption interval (e.g., T6).

For instance, in the (purely exemplary) embodiments discussed herein the sensor warm-up sequence comprises:
- supplying to the sensor said first heating power value for a first resumption interval (e.g., T1),
- supplying to the sensor a resumption power value (e.g., P2) for a second resumption interval (e.g., T2), the resumption power value different from the first heating power value,
- refraining from supplying power to the sensor for a third resumption interval (e.g., T6).

One or more embodiments may comprise supplying to the sensor said first heating power value—in the normal mode of, e.g., act 1002 in FIG. 3 or act 1050 of FIG. 7, and/or in other modes such as, e.g., the resumption mode discussed previously) with a supply profile comprising said first heating power value (P1) as a peak value and (at least one) second heating power value (e.g., P2) different from said first heating power value (see, e.g., FIG. 4).

One or more embodiments may relate to a circuit (e.g., 12) comprising:
- at least one input node (e.g., 22) configured to receive from a sensor (e.g., 10) a sensing signal (e.g., R) indicative of a sensed entity,
- at least one power node (e.g., 20) configured to power the sensor,
- processing circuitry (e.g., 14), coupled with the at least one input node and the at least one power node, the processing circuitry configured to perform the steps of the method according to one or more embodiments.

One or more embodiments may relate to a device (e.g., 1) comprising:
- at least one sensor (e.g., 10), such as a gas sensor, for example a metal oxide semiconductor gas sensor, producing a sensing signal indicative of sensed entity,
- a circuit (e.g., 12) according to one or more embodiments, arranged with the at least one input node coupled to the sensor to receive the sensing signal therefrom and the at least one power node coupled to the sensor for powering the sensor.

One or more embodiments may relate to a computer program product, loadable in the memory of the processing circuitry in a circuit or a device according to one or more embodiments and including software code portions for performing the method according to one or more embodiments when the product is run on the processing circuitry.

Without prejudice to the underlying principles, the details and embodiments may vary, even significantly, with respect to what has been disclosed by way of example only, without departing from the extent of protection.

The extent of protection is defined by the annexed claims.

The invention claimed is:

1. A method, comprising:
    driving a heating element of a gas sensor at a first heating power value;
    receiving from the gas sensor a sensing signal indicative of a sensed entity;
    detecting, as a function of the received sensing signal, onset of a sensor contamination condition;
    continuing driving the heating element of the gas sensor at said first heating power value if said detecting fails to indicate onset of the sensor contamination condition; and
    activating a protection mode if said detecting indicates onset of the sensor contamination condition, wherein activating the protection mode includes driving the heating element of the gas sensor at a second heating power value for a protection interval, wherein said second heating power value is lower than said first heating power value.

2. The method of claim 1, wherein activating said protection mode comprises:
    supplying to the heating element of the gas sensor said first heating power value for at least one respective time interval following said protection interval;
    checking whether a sensor contamination condition persists at the end of said at least one respective time interval;
    resuming supplying to the heating element of the gas sensor said first heating power value if said checking fails to indicate that the sensor contamination condition persists; and
    activating again said protection mode if said checking indicates that the sensor contamination condition persists.

3. The method of claim 1, further comprising:
    resuming supplying to the heating element of the gas sensor said first heating power value after activating the protection mode; and
    checking whether a sensor contamination condition persists as a result of activation of said protection mode;
    further comprising performing, prior to resuming supplying to the heating element of the gas sensor said first heating power value, a sensor warm-up sequence comprising:
        i) supplying to the heating element of the gas sensor said first heating power value for a resumption interval; and
        ii) refraining from supplying power to the heating element of the gas sensor for a further resumption interval.

4. The method of claim 1, further comprising supplying to the heating element of the gas sensor a supply profile comprising said first heating power value as a peak value and at least one second heating power value different from said first heating power value.

5. The method of claim 1, wherein the gas sensor is a heating metal oxide semiconductor gas sensor.

6. The method of claim 1, wherein activating said protection mode further includes refraining from supplying power to the heating element of the gas sensor for a further protection interval.

7. The method of claim 6, wherein said further protection interval is longer than said protection interval.

8. The method of claim 1:
    wherein the sensed entity of the sensing signal is indicative of a resistance value of the gas sensor and wherein driving the heating element of the gas sensor at the first heating power value comprises intermittently supplying to the heating element of the gas sensor the first heating power value for a plurality of time intervals;
    wherein detecting onset of the sensor contamination condition comprises:
        sensing, as a function of the sensing signal, a plurality of said resistance values of the gas sensor over the time intervals in said plurality of time intervals;
        calculating, as a function of the sensing signal, a plurality of slope values indicative of a behavior of the sensing signal over the time intervals in said plurality of time intervals;
        checking said plurality of resistance values and said plurality of slope values against a reference template; and
        declaring onset of the sensor contamination condition if said plurality of resistance values and said plurality of slope values fail to comply with said reference template.

9. The method of claim 8, further comprising:
    generating a plot of said plurality of slope values against said plurality of resistance values, wherein said plot is aligned with an alignment direction;
    checking whether said alignment direction matches with a reference alignment direction; and
    declaring onset of the sensor contamination condition if said alignment direction fails to match with said reference alignment direction.

10. The method of claim 9, further comprising:
    storing the alignment direction that leads to activating said protection mode as a result of detecting onset of the sensor contamination condition;
    intermittently supplying to the heating element of the gas sensor said first heating power value for a second plurality of time intervals following said protection interval;
    checking whether a sensor contamination condition persists at the end of said second plurality of time intervals by:
        sensing, as a function of the sensing signal from the gas sensor, a plurality of said resistance values of the gas sensor over said second plurality of time intervals;
        calculating, as a function of the sensing signal from the gas sensor, a plurality of slope values indicative of the behavior of the sensing signal over said second plurality of time intervals;
        generating a respective plot of said plurality of slope values against said plurality of resistance values for said second plurality of time intervals, wherein said respective plot is aligned with a respective alignment direction;
        comparing said respective alignment direction with said alignment direction stored; and
        declaring that the sensor contamination condition persists at the end of said second plurality of time intervals as a function of the result of said comparing.

11. The method of claim 10, wherein declaring that the sensor contamination condition persists at the end of said second plurality of time intervals is made if said respective alignment direction is either aligned with said stored alignment direction or diverges away from said reference alignment direction.

12. A method, comprising:
intermittently driving a heating element of a gas sensor at a first heating power value for a plurality of time intervals;
receiving from the gas sensor a sensing signal indicative of a sensed resistance;
detecting, as a function of the received sensing signal, onset of a sensor contamination condition; and
activating a protection mode if said detecting indicates onset of the sensor contamination condition;
wherein activating the protection mode comprises driving the heating element of the gas sensor at a second heating power value for a protection interval, wherein said second heating power value is lower than said first heating power value;
wherein detecting comprises:
sensing, as a function of the sensing signal, resistance values over said plurality of time intervals;
calculating, as a function of the sensing signal, slope values indicative of a behavior of the sensing signal over said plurality of time intervals;
checking said resistance values and said slope values against a reference template; and
signaling onset of the sensor contamination condition if said resistance values and said slope values fail to comply with said reference template.

13. The method of claim 12, wherein checking comprises:
generating a plot of said slope values against said resistance values, wherein said plot is aligned with an alignment direction; and
determining whether said alignment direction matches with a reference alignment direction; and
wherein signaling comprises declaring onset of the sensor contamination condition if said alignment direction fails to match with said reference alignment direction.

14. The method of claim 12, further comprising:
storing an alignment direction;
intermittently supplying to the heating element of the gas sensor said first heating power value for a second plurality of time intervals following said protection interval; and
determining whether a sensor contamination condition persists at the end of said second plurality of time intervals by:
sensing resistance values of the gas sensor over said second plurality of time intervals;
calculating, as a function of the sensing signal, slope values indicative of the behavior of the sensing signal over said second plurality of time intervals;
generating a respective plot of said slope values against said resistance values for said second plurality of time intervals, wherein said respective plot is aligned with a respective alignment direction;
comparing said respective alignment direction with said stored alignment direction; and
indicating that the sensor contamination condition persists at the end of said second plurality of time intervals if said respective alignment direction is either aligned with said stored alignment direction or diverges away from said reference alignment direction.

15. The method of claim 12, wherein activating said protection mode comprises:
supplying to the heating element of the gas sensor said first heating power value for at least one respective time interval following said protection interval;
checking whether a contamination condition persists at the end of said at least one respective time interval;
resuming supplying to the heating element of the gas sensor said first heating power value if said checking fails to indicate that the sensor contamination condition persists; and
activating again said protection mode if said checking indicates that the sensor contamination condition persists.

16. The method of claim 12, wherein the gas sensor is a heating metal oxide semiconductor gas sensor.

17. A method, comprising:
intermittently supplying a heating element of a gas sensor at a first heating power value for a plurality of time intervals;
receiving from the gas sensor a sensing signal indicative of a sensed entity;
detecting, as a function of the received sensing signal, onset of a sensor contamination condition; and
activating a protection mode if said detecting indicates onset of the sensor contamination condition;
wherein activating the protection mode comprises driving the heating element of the gas sensor at a second heating power value for a protection interval, wherein said second heating power value is lower than said first heating power value;
wherein detecting comprises:
calculating, as a function of the received sensing signal, slope values indicative of a behavior of the sensing signal over said plurality of time intervals;
checking said slope values against a reference template; and
declaring onset of the sensor contamination condition if said slope values fail to comply with said reference template.

18. The method of claim 17, wherein said protection mode further comprises refraining from supplying power to the heating element of the gas sensor for a further protection interval.

19. The method of claim 18, wherein said further protection interval is longer than said protection interval.

20. The method of claim 17, wherein detecting onset of the sensor contamination condition further comprises:
sensing, as a function of the sensing signal, resistance values of the gas sensor over said plurality of time intervals;
checking said resistance values against the reference template; and
declaring onset of the sensor contamination condition if said resistance values fail to comply with said reference template.

21. The method of claim 20, further comprising:
generating a plot of said slope values against said resistance values, wherein said plot is aligned with an alignment direction;
checking whether said alignment direction matches with a reference alignment direction; and
declaring onset of the sensor contamination condition if said alignment direction fails to match with said reference alignment direction.

22. A method, comprising:
intermittently driving a heating element of a gas sensor at a first heating power value for a plurality of time intervals;
receiving from the gas sensor a sensing signal indicative of sensor resistance value;
detecting, as a function of the received sensing signal, onset of a sensor contamination condition; and
activating a protection mode if said detecting indicates onset of the sensor contamination condition;
wherein activating the protection mode comprises driving the heating element of the gas sensor at a second heating power value for a protection interval, wherein said second heating power value is lower than said first heating power value;
wherein detecting comprises:
  calculating, as a function of the received sensing signal, slope values indicative of a behavior of the sensing signal over said plurality of time intervals;
  generating a plot of said slope values against sensor resistance value, wherein said respective plot is aligned with an alignment direction;
  comparing said alignment direction with a reference alignment direction; and
  indicating onset of the sensor contamination condition if said alignment direction fails to match with said reference alignment direction.

23. The method of claim 22, further comprising:
storing the alignment direction;
intermittently supplying to the heating element of the gas sensor said first heating power value over a further plurality of time intervals following said protection interval; and
determining whether a sensor contamination condition persists at the end of said further plurality of time intervals by:
  calculating, as a function of the sensing signal, slope values indicative of the behavior of the sensing signal over the further plurality of time intervals;
  generating a respective plot of said slope values against sensor resistance value, wherein said respective plot is aligned with a respective alignment direction;
  comparing said respective alignment direction with said stored alignment direction; and
  indicating that the sensor contamination condition persists at the end of said further plurality of time intervals if said respective alignment direction is aligned with said stored alignment direction.

24. The method of claim 22, further comprising:
storing the alignment direction;
intermittently supplying to the heating element of the gas sensor said first heating power value over a further plurality of time intervals following said protection interval; and
determining whether a sensor contamination condition persists at the end of said further plurality of time intervals by:
  calculating, as a function of the sensing signal, slope values indicative of the behavior of the sensing signal over the further plurality of time intervals;
  generating a respective plot of said slope values against sensor resistance value, wherein said respective plot is aligned with a respective alignment direction;
  comparing said respective alignment direction with said stored alignment direction; and
  indicating that the sensor contamination condition persists at the end of said further plurality of time intervals if said respective alignment direction diverges away from said reference alignment direction.

25. The method of claim 22, wherein activating said protection mode comprises:
  supplying to the heating element of the gas sensor said first heating power value over a further time following said protection interval;
  checking whether a sensor contamination condition persists at the end of said further time;
  resuming supplying to the heating element of the gas sensor said first heating power value if said checking fails to indicate that the sensor contamination condition persists; and
  activating again said protection mode if said checking indicates that the sensor contamination condition persists.

26. The method of claim 22, wherein the gas sensor is a heating metal oxide semiconductor gas sensor.

* * * * *